United States Patent [19]

Troutner

[11] Patent Number: 4,490,135
[45] Date of Patent: Dec. 25, 1984

[54] SINGLE NEEDLE ALTERNATING BLOOD FLOW SYSTEM

[75] Inventor: Vernon H. Troutner, St. Petersburg, Fla.

[73] Assignee: Extracorporeal Medical Specialties, Inc., King of Prussia, Pa.

[21] Appl. No.: 423,380

[22] Filed: Sep. 24, 1982

[51] Int. Cl.³ .............................................. A61M 1/03
[52] U.S. Cl. ........................................ 604/5; 604/31; 604/52; 604/67; 128/DIG. 13
[58] Field of Search ........................................ 604/4–6, 604/27, 28, 29, 31, 34, 51, 52, 66, 67, 153, 118, 246; 128/DIG. 13; 417/476, 477; 138/30

[56] References Cited

U.S. PATENT DOCUMENTS

| | | | |
|---|---|---|---|
| 3,140,714 | 7/1964 | Murphy, Jr. et al. | 604/6 |
| 3,756,234 | 9/1973 | Kopp | 604/5 |
| 3,830,234 | 8/1974 | Kopp | 604/5 |
| 3,881,483 | 5/1975 | Sausse | 604/4 |
| 3,964,479 | 6/1976 | Boag et al. | 604/5 X |
| 4,063,554 | 12/1977 | Willock et al. | 604/5 X |
| 4,146,028 | 3/1979 | LeFevre | 138/30 |
| 4,218,197 | 8/1980 | Meyer et al. | 417/477 X |
| 4,228,930 | 10/1980 | Hogan | 417/477 X |
| 4,231,366 | 11/1980 | Schael | 604/4 |
| 4,385,630 | 5/1983 | Gilcher et al. | 604/67 X |

Primary Examiner—Stephen C. Pellegrino
Attorney, Agent, or Firm—Mark A. Hofer

[57] ABSTRACT

A two-pump single needle hemodialysis system is provided in which a flexible blood accumulator bag is located between the dialyzer and the second, venous blood pump. The accumulator bag is filled as the first, arterial blood pump is operated. Blood is pumped through the dialyzer and into the bag until the bag is full and taut. At this time, a rise in pressure is detected and the venous blood pump is activated to withdraw blood from the accumulator bag. The use of the accumulator bag assures that low blood pressures are maintained in the system.

12 Claims, 5 Drawing Figures

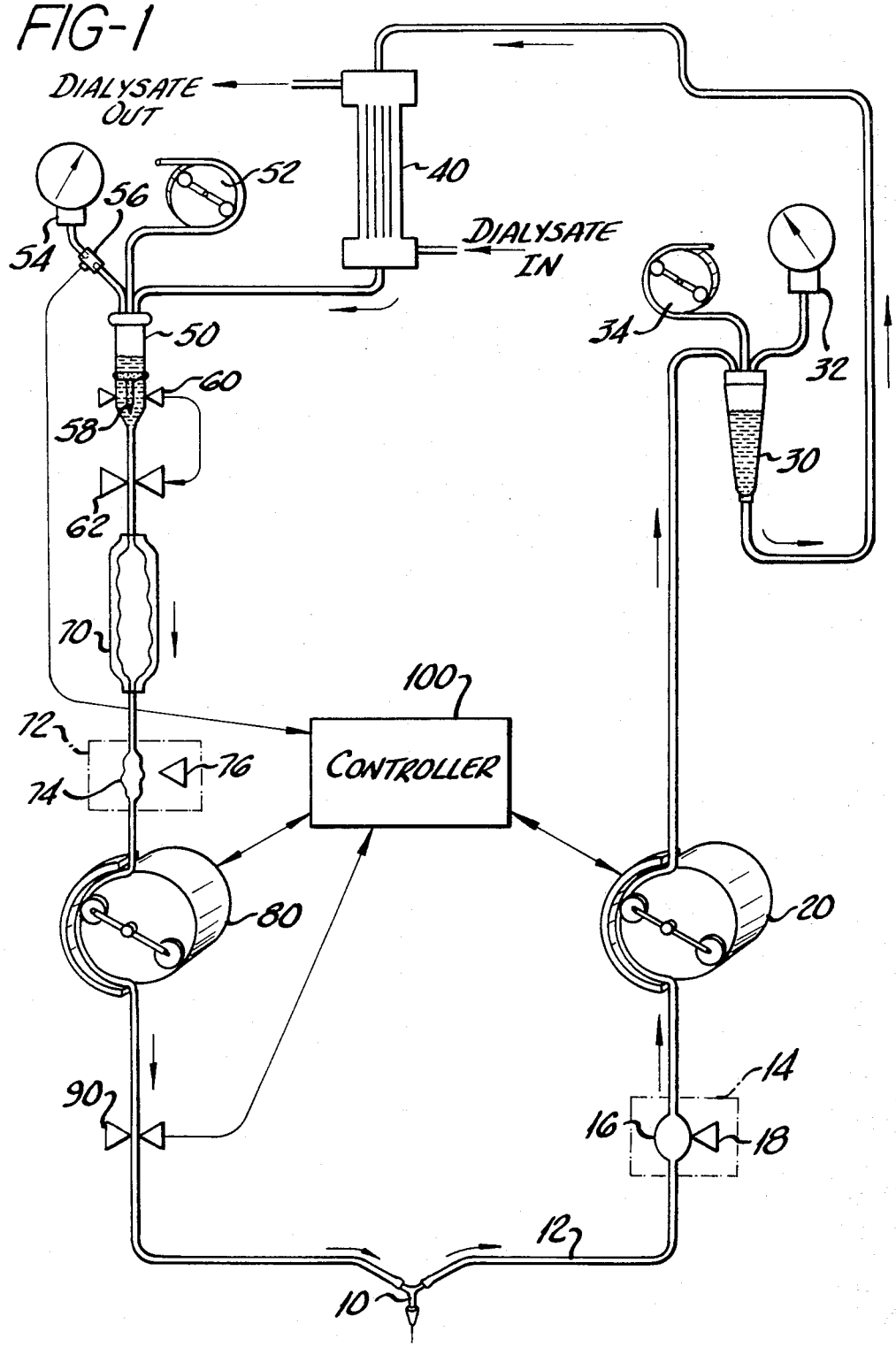

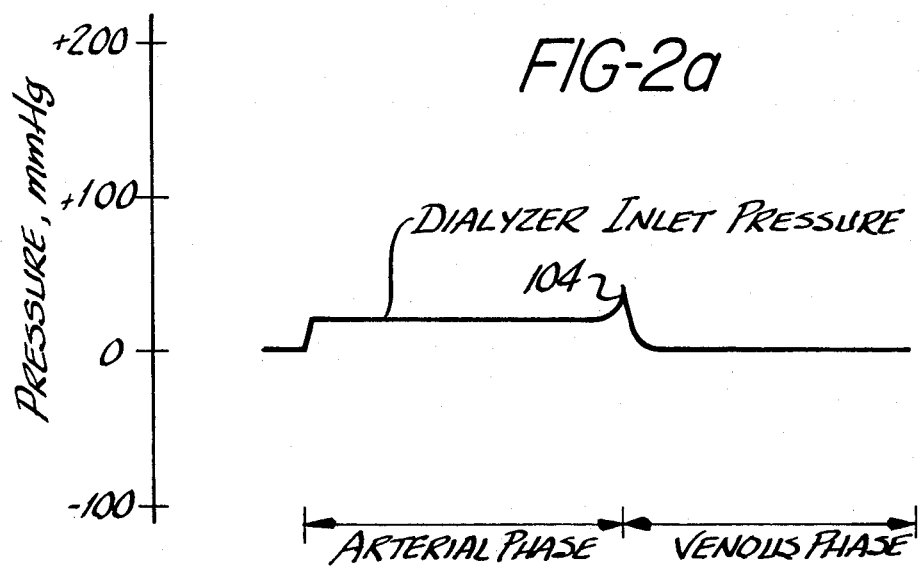
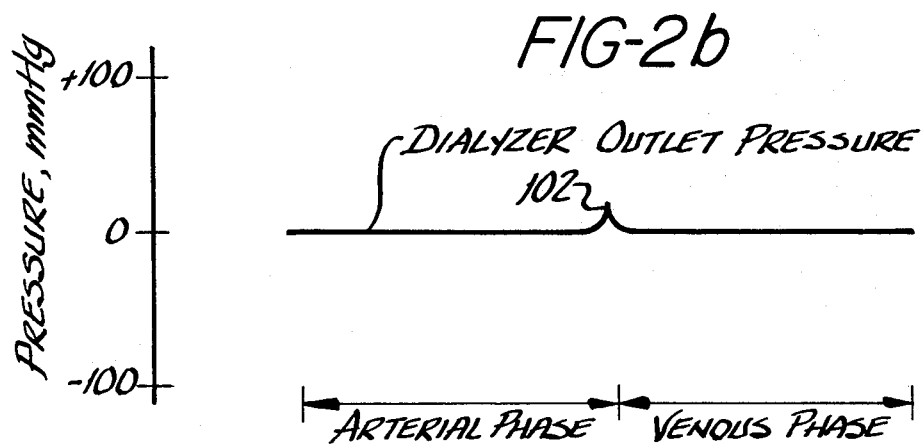

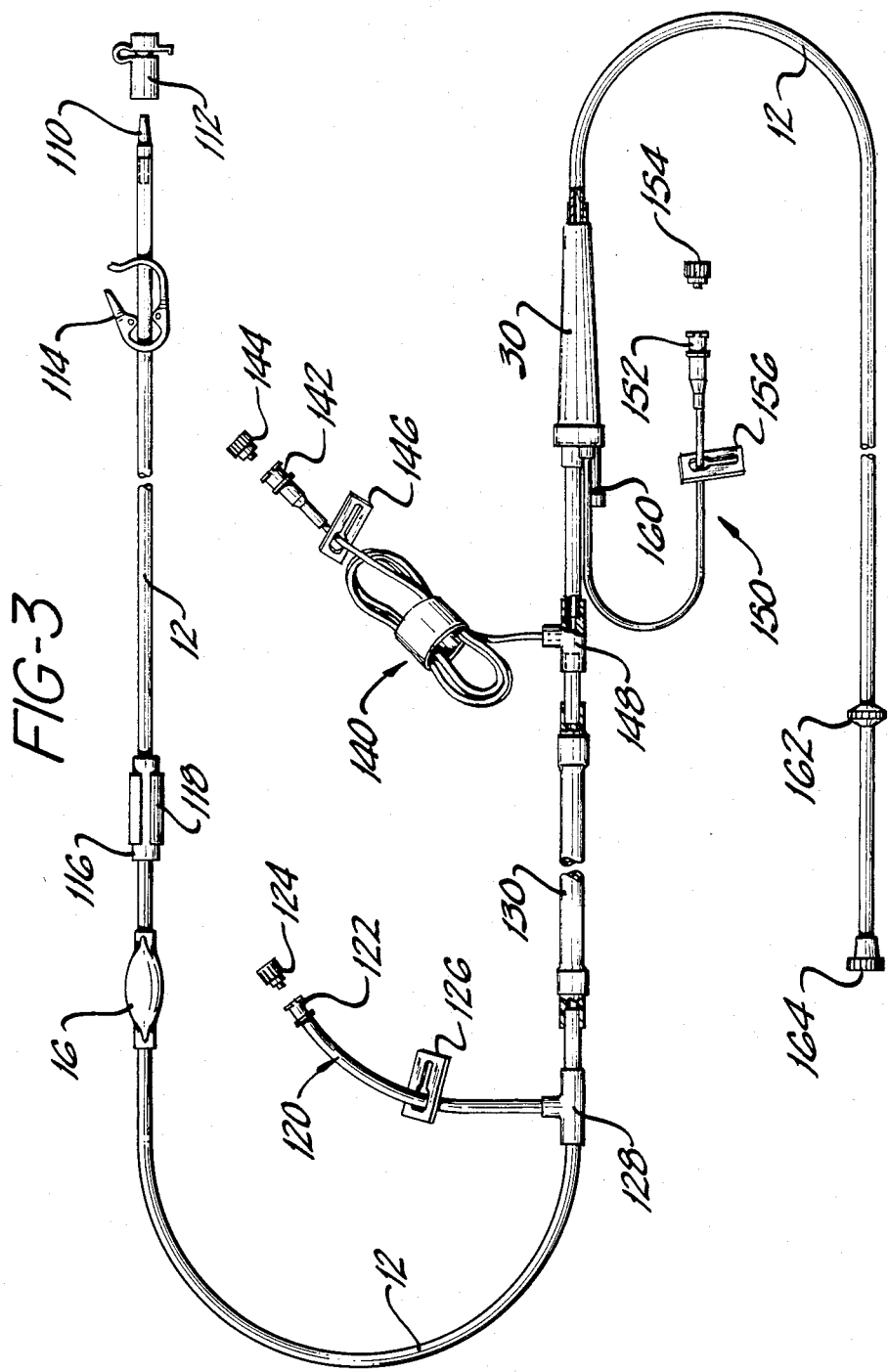

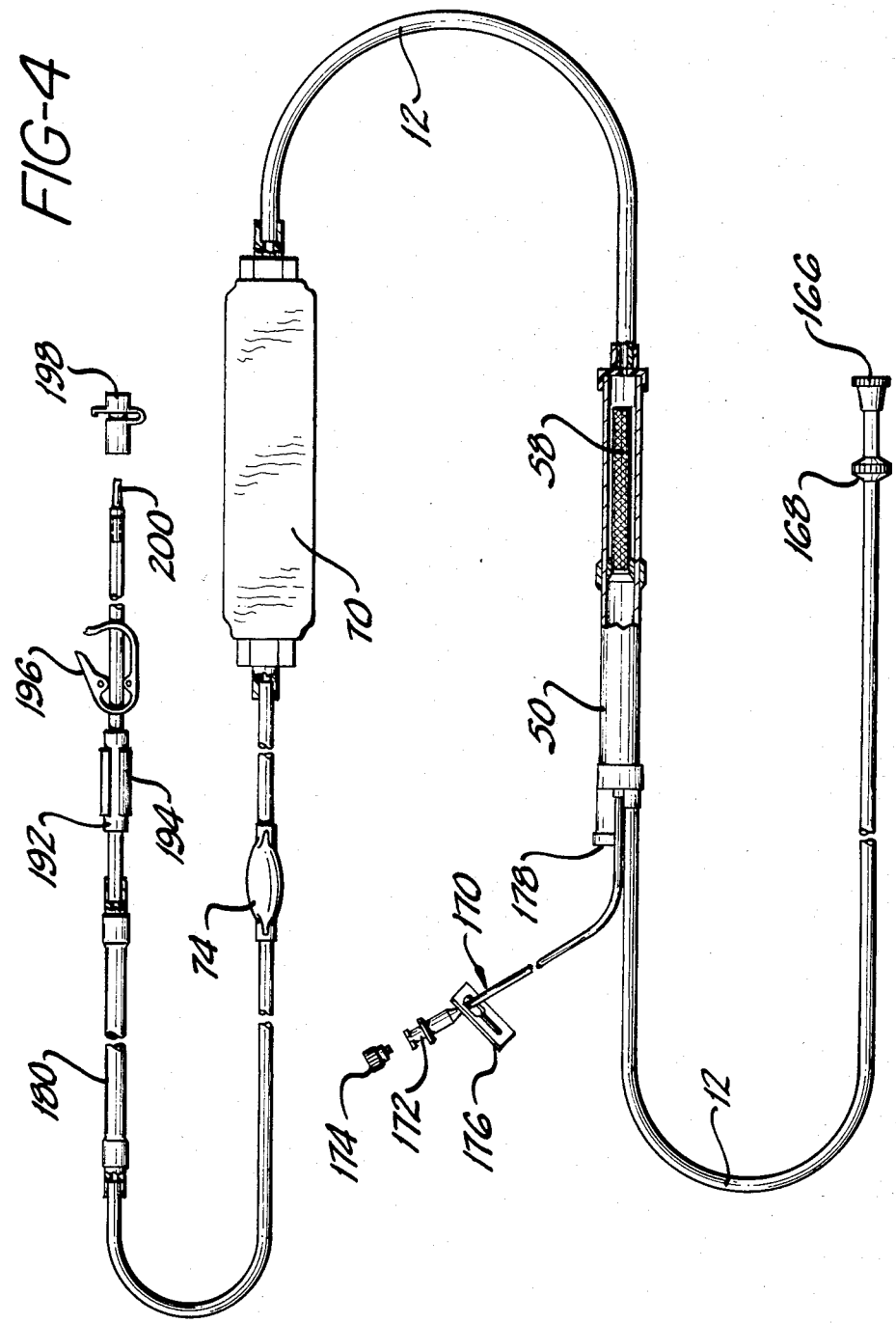

SINGLE NEEDLE ALTERNATING BLOOD FLOW SYSTEM

This invention relates to single needle alternating blood flow systems and in particular, to single needle hemodialysis systems.

Hemodialysis blood flow systems are employed as a therapeutic measure when a patient's kidneys no longer perform their blood purifying function by reason of disease, removal or other malfunction. Kidney failure results in the accumulation of toxic wastes in the patient's blood. Unless measures are taken to remove these wastes, the patient will experience potentially fatal uremic poisoning. Uremic poisoning may be prevented through the use of hemodialysis, by which blood is drawn from the patient and circulated through a dialyzer. In the dialyzer, the blood is separated from a specially treated dialysate fluid by a membrane which has pores of microscopic size through which waste products from the blood may pass. The microscopic pores are too small, however, to permit the passage of blood cells, proteins, and other essential elements of the blood through the membrane. The waste products thus diffuse into the dialysate fluid and are removed from the patient's blood. The purified blood is then returned to the patient's body.

In many conventional hemodialysis systems, such as the Single Patient System (SPS) Model DM-350, produced by Extracorporeal Inc. of King of Prussia, Pa., blood is extracted from the patient through a first arterial venipuncture, which may typically be formed in a cannulation procedure. The blood is then processed by the SPS system and returned to the patient's body through a second, venous venipuncture, which may also comprise a cannula. The cannulated venipunctures, however, may not be used indefinitely. Over time, the cannulas may be gradually extruded at the exit site of the patient's body, or infection may occur. In addition, the skin over the veins will thicken after repeated hemodialysis. It then becomes necessary to surgically provide new venipunctures in the patient's body for continued hemodialysis.

Recently, the need for two venipunctures in hemodialysis has been obviated by the development of single needle hemodialysis systems. In these systems, blood is extracted from and returned to the patient's body through a single needle with a Y-shaped junction. The patient is generally prepared for hemodialysis by the surgical implantation of an arteriovenous fistula, which joins an artery with a nearby vein. The diversion of arterial blood into the vein causes the vein to become enlarged, permitting relatively easy insertion of the single needle into the arterialized vein, through which an adequate blood flow for hemodialysis is developed. It has been found that fistula vessels are less traumatized by the single needle technique, and that patients benefit psychologically from the reduced number of venipunctures.

In a typical single needle hemodialysis system, blood is alternately cycled from and to the patient's circulatory system by a single blood pump, or by arterial and venous blood pumps, respectively. During the first, or arterial, phase of operation, blood is drawn from the patient and pumped into the dialysis system by the arterial blood pump. Blood is prevented from returning to the needle by the closure of a valve located between the outlet of the arterial pump and the needle, or through clamping action of the venous blood pump. Blood pressure within the system builds until a time at which the arterial pump is turned off, the valve is opened, or the venous pump in a two-pump system is turned on to pump the blood out of the dialysis system and back to the fistula. During this second, or venous, phase of operation, the pressure of the blood in the dialysis system drops substantially. Eventually a point is reached at which the venous pump is turned off, and the cycle repeats.

The cyclic changeover between the arterial and venous phases may be accomplished by controlling the times of operation of the two pumps, or by activating the pumps in response to the attainment of preset pressure limits within the system. Typically, the arterial phase is characterized by the buildup of a high blood pressure within the system. This can result in undesirable high system stress, mandatory high ultrafiltration within the dialyzer, and attendant safety concerns. On the other hand, blood pressure is subject to a precipitous decline during the venous phase as the blood is pumped back to the fistula. The attainment of a very low or negative blood pressure in the system can reverse the necessary blood to dialysate pressure differential across the dialyzer membrane (TMP), and can also undesirably result in blood foaming and the mixing of venous and arterial blood at the single needle junction. Accordingly, it is desirable to reduce or eliminate these adverse effects of blood pressure differential in a single needle hemodialysis system.

In accordance with the principles of the present invention, a single needle hemodialysis system is provided which maintains a substantially constant pressure reference in the blood tubing system. During the arterial phase of operation, blood is drawn through the single needle and is pumped through a dialyzer and into a flexible accumulator. The accumulator expands readily as it is filled, thereby generating substantially no back pressure as it is being filled. The only significant pressure change is the pressure drop resulting from blood flow through the dialyzer. Venous pressure therefore remains at approximately zero gage until the expansive limits of the accumulator are reached. At this time, a pressure rise is detected, the arterial phase is terminated, and the venous phase is initiated. Blood is withdrawn from the accumulator, which collapses as the blood is returned through the single needle. Thus, the pressure in the dialyzer remains substantially at zero gage as the blood is returned to the patient. When a sufficient amount of blood has been returned to the patient, the venous cycle is terminated and the cycle repeats.

It may be seen that this technique results in substantial blood flow through the dialyzer during the arterial phase of operation, and the maintenance of substantially zero gage blood pressure in the dialyzer during the venous phase. The blood pressure differential between the two phases of operation is kept at a very low level.

In the drawings:

FIG. 1 shows the blood circulation path of a single needle hemodialysis system constructed in accordance with the principles of the present invention; and FIGS. 2a and 2b graphically represent blood pressures at the inlet and outlet of the dialyzer of FIG. 1;

FIG. 3 illustrates an arterial line blood tubing set suitable for use in the arrangement of FIG. 1; and FIG. 4 illustrates a venous line blood tubing set suitable for use in the arrangement of FIG. 1.

Referring to FIG. 1, the blood flow path of a hemodialysis system is shown, including a single needle 10 suitable for the transfer of blood from and to a patient. In FIG. 1, the arrows indicate the direction of the flow of blood through the system.

From the single needle 10, blood flows through the blood tubing 12 to a negative pressure pillow switch 14. The pillow switch 14 includes a pillow-like section of tubing 16 and a sensor or switch 18 which is responsive to a relaxation of pressure in the pillow-like section 16. When the pillow pressure declines below a certain level the sensor or switch responds by initiating a system alarm as well as other procedures which interrupt the operation of the system.

From the pillow switch 14 the blood tubing is connected through an arterial roller blood pump 20. The arterial blood pump 20 operates under control of a controller 100, as will be described subsequently. The blood tubing is then connected to a post-pump arterial drip chamber 30 which collects blood and accommodates the connection of various gauges to the system. The pressure in the drip chamber 30 is monitored by an arterial mechanical gauge 32 with alarm contacts. The blood level within the chamber 30 may be varied through the operation of a blood level adjust roller pump 34, by which air may be added to or subtracted from the chamber. The outlet of the drip chamber 30 is connected by blood tubing to the inlet of a capillary dialyzer 40. In the dialyzer, impurities in the blood pass through the dialyzer membrane and into dialysate fluid, which flows into and out of the dialyzer through separate ports under control of a dialysate preparation system (not shown).

Purified blood flows out of the dialyzer 40 and into a venous drip chamber 50. The pressure within the venous drip chamber 50 is monitored by a mechanical venous pressure gauge 54 with alarm contacts. A second blood level adjust pump 52 is connected to the drip chamber 50 to add or subtract air from the chamber, thereby adjusting the blood level within the chamber. In a tubing line between the venous drip chamber 50 and the venous pressure gauge 54 is a solid state pressure transducer 56 which controls the cycling of the blood pumps and also provides another monitor of venous blood pressure. The venous drip chamber 50 further includes a filter 58 located within the chamber.

An air/foam detector 60 is located next to the venous drip chamber 50. The detector 60 ultrasonically or optically detects the presence of an abnormal amount of air or foam in the blood and also monitors the blood level in the chamber 50. The detector responds to the occurence of such an abnormality by activating a clamp 62, which clamps the blood tubing closed to prevent the pumping of foam and air bubbles into the patient's circulatory system.

The blood tubing is then connected to the inlet of a vinyl accumulator bag 70. The outlet of the accumulator bag 70 is coupled to a positive pressure pillow switch 72, which may be merely an extension of the accumulator bag 70 or, as shown in FIG. 1, may include its own pillow-shaped tubing section 74. Abnormal expansion of the pillow-shaped section 74 in response to an undesirable buildup of blood pressure causes the sensor or switch portion 76 to set off an alarm and to interrupt system operation.

From the pillow switch 72 the blood tubing passes through a venous roller blood pump 80 which is operated under control of the controller 100. The blood tubing then passes through a second air/foam detector 90, which is connected into the system alarm by the controller 100. Finally, the blood tubing is connected to the needle 10 to return the purified blood to the patient's circulatory system.

In operation, the arterial blood pump 20 of FIG. 1 is activated by the controller 100 to begin withdrawing blood from the patient through the needle 10. The negative pressure pillow switch safeguards against the withdrawal of blood at too great a rate, as indicated by the development of a negative pressure at the switch. Withdrawal of blood at too great a rate by the arterial pump can lead to collapse of the patient's fistula, blood foaming or recirculation of purified blood at the needle junction. The pillow switch also guards against any blockage of blood flow in the fistula and needle, which condition activates a system shutdown.

The patient's blood is pumped through the blood tubing 12, the arterial drip chamber 30, and into the dialyzer 40. The flow of blood is virtually unimpeded up to the dialyzer, at which point the pressure developed by the arterial pump forces the blood through the capillaries of the dialyzer. The dialyzer consitutes the only significant pressure drop between the arterial blood pump 20 and the accumulator bag. This pressure drop will vary with the type of dialyzer. FIG. 2a illustrates the typical inlet pressure of a capillary-type dialyzer. During the arterial phase of operation, when the arterial blood pump 20 is running, the dialyzer inlet pressure in this example is seen to remain substantially at 20-25 mm relative to atmospheric pressure, which would be indicated on the arterial gage 32.

At the outlet of the dialyzer, however, blood pressure remains substantially at 0 mm (gauge), as shown in FIG. 2b. This is because the purified blood is free to flow into the venous drip chamber 50, and then into the accumulator bag 70. The accumulator bag is initially empty, and easily fills with blood from the drip chamber, since the outside of the bag is referenced to atmospheric pressure. Thus, as the accumulator bag fills, it produces substantially no back pressure which would impede the flow of blood out of the dialyzer. Furthermore, since the accumulator bag is referenced to atmospheric pressure, the pressure sensing devices at the outlet side of the dialyzer, such as the venous pressure gauge 54 and the pressure transducer 56, can indicate the accumulator bag pressure directly by being similarly referenced to atmospheric pressure.

The accumulator bag fills freely with blood until full, at which time its expansive limits are approached and the pressure in the accumulator bag and venous drip chamber begins to rise, as indicated at 102 in FIG. 2b. This rise in pressure is translated back to the inlet side of the dialyzer, as shown at 104 of FIG. 2a. The rise in pressure is indicated by both the arterial and venous mechanical gages 32 and 54, and is also sensed by the solid state pressure transducer 56. The transducer 56 sends a signal to the controller 100. The controller 100, which may include a microprocessor, for instance, responds to the attainment of a predetermined pressure level at the dialyzer outlet, in this example, 20 mm, by stopping operation of the arterial blood pump and initiating operation of the venous blood pump 80. The positive pressure pillow switch 72 guards against the attainment of an unusually high venous pressure by shutting down the system if such pressures are approached.

The venous blood pump 80 is operated for a given number of cycles to remove the blood from the accumulator bag and return it to the patient's system. Pump cycles may be used as the measure of this venous phase of operation since each pump cycle corresponds to the pumping of a known volume of blood. The number of pump cycles required to empty the accumulator bag may also be determined since the capacity of the bag when full is a known quantity, the blood levels in the drip chambers 30 and 50 may be controlled by the blood level adjust pumps 34 and 52, and the blood tubing system is essentially noncompliant and has a predictable blood capacity.

As blood is returned to the patient the venous pressure at the outlet of the dialyzer rapidly falls back to zero mm gauge, as shown in FIG. 2b, as the accumulator bag quickly relaxes. At the same time, the blood pressure at the inlet side of the dialyzer drops back toward zero gage pressure since the arterial blood pump is turned off. This means that blood flow through the dialyzer occurs primarily during the arterial phase of the system, when the arterial blood pump is forcing blood through the dialyzer. Since the dialyzer pressure does not go below zero as the accumulator bag is emptied, undesirable negative transmembrane pressures are not produced in the system. While the blood is being returned to the patient during the venous phase, the air/foam detector 90 monitors the returning blood and alerts the controller 100 if an undesirable amount of air or foam is contained in the blood. When the desired amount of blood has been returned to the patient, the controller terminates the venous phase by stopping the blood pump 80 and initiates operation of the arterial pump 20 to begin another arterial phase of operation. The phasing of blood pump operation is described more fully in U.S. patent application Ser. No. 423,378, entitled "DUAL PHASE BLOOD FLOW SYSTEM AND METHOD OF OPERATION".

As discussed above, the pressure within the flexible accumulator bag 70 remains at zero relative to atmospheric pressure until the time at which the bag becomes full and taut. At that time the venous pressure exhibits a rapid, detectable rise. In order for the pressure rise to be relatively rapid and easily identifiable, it is desirable for the accumulator bag to resist increases in volume when full, as by exhibiting minimal or zero stretch characteristics. The bag should have a maximum capacity, and hence it should not ballon or stretch when full. However, a minimal stretch characteristic means that the bag could be susceptible to rupturing if pumping phase changeover does not occur promptly. Accordingly, in accordance with the principles of a further aspect of the present invention, the accumulator bag 70 in FIG. 1 may be located in a rigid tube 78 made of a plastic material, which will surround the bag 70 and prevent rupturing at the bag seams. Locating the bag in the tube will increase its burst pressure from 10 lbs. to 25 lbs., for example. Alternately, the rigid tube 78 may be replaced with a non-stretch jacket, mylar sleeve or sock, which performs the same restraining function. As a further alternative, a specially manufactured bag may be constructed to have exceptional burst-resistance characteristics, as by the use of a fiber reinforced bag, for instance. A bag with a higher burst pressure provides an extra measure of safety in the arrangement of FIG. 1.

An arterial line blood set suitable for use in the arrangement of FIG. 1 is illustrated in detail in FIG. 3. A male luer 110 is connected to the end of a tubing section 12. The male luer 110 connects to one segment of the single needle 10 of FIG. 1, and is protected when not in use by a hinged cap 112. A ratchet clamp 114 is located on the tubing section following the male luer.

Following the ratchet clamp is a puncture site, including a latex sleeve 116 and an injection site guard 118. Blood samples may be taken from the puncture site by inserting a hypodermic needle through the latex sleeve 116 and into the tubing section 12. The latex sleeve will provide a seal after the hypodermic needle is withdrawn. The negative pressure pillow assembly 16 is located in the blood tubing line following the puncture site.

An administration line assembly 120 is connected to the blood tubing set by a tee-shaped connector 128. A female luer is capped by a luer guard cap 124 when not in use. A slide clamp 126 is located on the tubing section of the administration line. The administration line may be used to inject solutions such as saline into the blood line.

The arterial blood pump segment 130 follows the administration line. The pump segment 130 is looped through the arterial roller pump 20 and generally has a larger diameter than the normal blood tubing segments 12. In this example, the arterial pump segment 130 has an inside diameter of 5/16 of an inch.

A heparin administration line 140 is coupled to the blood tubing set by a tee-shaped connector 148 following the pump segment 130. A female luer 142 with an end cap 144 is connected at the end of the heparin line. A slide clamp 146 is located on the heparin line tube segment. The blood tubing next goes to the arterial drip chamber 30.

Extending from the top of the arterial drip chamber 30 is a manometer gauge line assembly 150 for connection to the arterial pressure gauge 32 and the level adjust pump 34. The manometer line assembly 150 is terminated by a female luer 152 with a protective cap 154. A slide clamp 156 is also located on the gauge line. An access site is also located at the top of the drip chamber 30, and is capped by a rubber dam or diaphragm 160.

At the end of the blood tubing segment extending from the bottom of the arterial drip chamber 30 is a flare plug 164, which is used to seal the end of the tubing segment when not in use. A luer collar 162 is located about the tubing set near the end and is used to clamp the blood tubing set onto the inlet of the dialyzer.

FIG. 4 illustrates a venous line blood set suitable for use in the arrangement of FIG. 1. Flare plug 166 and leur collar 168 are located at the end of the line which connects to the output to the dialyzer 40. The blood tubing segment then goes to the top of the venous drip chamber 50. Extending from the top of the venous drip chamber 50 is an access site capped with a rubber dam 178, and a manometer line assembly 170 for connection to the solid state pressure transducer 56 and the venous pressure gauge 54 of FIG. 1. The manometer line assembly 170 includes a female luer guard 174, and a slide clamp 176. When used in the arrangement of FIG. 1 the female luer 172 connects to a tubing segment which includes the pressure transducer 56 and a line which leads to the venous pressure gauge 54. Also located in this line would be a tee-shaped connector which connects to a tubing segment leading to the level adjust pump 52.

A blood tubing segment 12 leads from the bottom of the venous drip chamber 50 to the flexible accumulator bag 70. From the outlet of the accumulator bag 70, the blood tubing leads to a positive pressure pillow assembly 74, and thence to a venous pump segment 180. The venous pump segment 180, like the arterial pump segment 130 of FIG. 3, has a 5/16 inch interior diameter in this example.

From the venous pump segment 180 the blood tubing goes through a venous puncture site, including a latex sleeve 192 and an injection site guard 194. A ratchet clamp 196 is coupled around the line following the puncture site. The venous line is terminated by a male luer 200, which will connect with the needle 10. The male luer 200 is protected when not in use by a hinged luer cap 198.

I claim:

1. A hemodialysis system for treatment of a patient comprising:
   means for withdrawing blood from said patient;
   an arterial blood pump having an input coupled to said withdrawing means and an output;
   a dialyzer, having an input coupled to the output of said arterial blood pump and an output, for purifying blood flowing therethrough;
   a blood accumulator having an input coupled to the output of said dialyzer and an output;
   a venous blood pump having an input coupled to the output of said accumulator and an output;
   means, coupled to the output of said venous blood pump, for returning purified blood to said patient; and
   wherein said blood accumulator is flexible and the outside of said flexible accumulator is exposed to atmospheric pressure so as to reference blood pressure within said accumulator to atmospheric pressure whereby substantially no back pressure is generated during operation of said arterial pump until the accumulator reaches its expansive limits.

2. A hemodialysis system for treatment of a patient comprising:
   means for withdrawing blood from said patient;
   an arterial blood pump having an input coupled to said withdrawing means and an output;
   a dialyzer, having an input coupled to the output of said arterial blood pump and an output, for purifying blood flowing therethrough;
   a blood accumulator having an input coupled to the output of said dialyzer and an output;
   non-compliant means surrounding said accumulator for preventing expansion of said accumulator beyond a given size;
   a venous blood pump having an input coupled to the output of said accumulator and an output;
   means, coupled to the output of said venous blood pump, for returning purified blood to said patient; and
   wherein said blood accumulator is flexible and exposed to atmospheric pressure so at to reference blood pressure within said accumulator to atmospheric pressure whereby substantially no back pressure is generated during operation of said arterial pump until the accumulator reaches its expansive limits.

3. The arrangement of claim 2, wherein said non-compliant means comprises a mylar sleeve.

4. The arrangement of claims 1 or 2, wherein said first and last recited means comprise legs of a hollow needle with a Y-shaped junction.

5. The arrangement of claims 1 or 2, wherein said flexible blood accumulator comprises a compliant vinyl bag.

6. The arrangement of claims 1 or 2 further comprising:
   a post-arterial pump drip chamber coupled between said output of said arterial blood pump and said input of said dialyzer; and
   a venous drip chamber coupled between said output of said dialyzer and said input of said flexible blood accumulator.

7. A blood tubing set for use in a dual pump, single needle hemodialysis system the improvement therein comprising a flexible blood accumulator bag exposed to atmospheric pressure so as to reference blood pressure within said accumulator bag to atmospheric pressure whereby substantially no back pressure is generated during operation until the accumulator bag reaches its expansive limits, said blood tubing set for said improved dialysis system comprising:
   an arterial blood tubing set including
      an arterial male luer;
      an arterial pressure pillow coupled to said arterial male luer by a tubing segment;
      an arterial blood pump segment coupled to said arterial pressure pillow by a tubing segment; and
      an arterial luer collar mounted on a further tubing segment, said further tubing segment being coupled to said arterial blood pump segment; and
   a venous blood tubing set including
      a venous luer collar mounted on a first venous tubing segment;
      said flexible blood accumulator bag having a first end, and a second end coupled to said first venous tubing segment;
      a venous pressure pillow connected to said first end of said accumulator bag by a tubing segment;
      a venous blood pump segment coupled to said venous pressure pillow by a tubing segment; and
      a venous male luer coupled to said venous blood pump segment by a tubing segment.

8. An arterial blood tubing set for use in a dual pump, single needle hemodialysis system the improvement therein comprising a flexible blood accumulator exposed to atmospheric pressure so as to reference blood pressure within said accumulator to atmospheric pressure whereby substantially no back pressure is generated during operation until the accumulator reaches its expansive limits, said arterial blood tubing set for said improved dialysis system comprising:
   an arterial male luer;
   an arterial pressure pillow coupled to said arterial male luer by a tubing segment;
   an arterial blood pump segment coupled to said arterial pressure pillow by a tubing segment;
   a post-arterial pump drip chamber coupled to said arterial blood pump segment by a tubing segment; and
   an arterial luer collar mounted on a further tubing segment, said further tubing segment being coupled to said drip chamber whereby, said arterial blood tubing set is adapted for use with a venous blood tubing set having said flexible blood accumulator.

9. A venous blood tubing set for use in a dual pump, single needle hemodialysis system the improvement therein comprising a flexible blood accumulator bag exposed to atmospheric pressure so as to reference blood pressure within said accumulator bag to atmospheric pressure whereby substantially no back pressure is generated during operation until the accumulator bag reaches its expansive limits, said blood tubing set for said improved dialysis system comprising:

- a venous luer collar mounted on a first venous tubing segment;
- a venous drip chamber having an input coupled to said first venous tubing segment and an output;
- said flexible blood accumulator bag having an input coupled to said output of said drip chamber by a tubing segment and having an output;
- a venous pressure pillow coupled to said output of said accumulator bag by a tubing segment;
- a venous blood pump segment coupled to said second venous pillow by a tubing segment; and
- a male luer coupled to said venous blood pump segment by a tubing segment.

10. The arrangement of claims 7 or 9, further comprising means, coupled between said venous luer collar and said accumulator bag, for connecting a pressure transducer to said blood tubing set.

11. The arrangement of claims 7 or 8, further comprising means, coupled between said arterial blood pump segment and said arterial luer collar, for connecting said blood tubing set to a pressure gauge.

12. The arrangement of claims 7 or 8, further comprising a heparin administration line coupled to said blood tubing set between said arterial blood pump segment and said arterial luer collar.

* * * * *